(12) United States Patent
Grant et al.

(10) Patent No.: US 8,510,061 B2
(45) Date of Patent: Aug. 13, 2013

(54) METHODS, SYSTEMS, AND COMPUTER READABLE MEDIA FOR WIRELESS CRACK DETECTION AND MONITORING

(75) Inventors: Edward Grant, Raleigh, NC (US); Matthew David Craver, Raleigh, NC (US); Carey Merritt, Oak Ridge, NC (US); Kyle Luthy, San Diego, CA (US); Jonathan Simmons, Millersville, MD (US); Kyle Roberts, Raleigh, NC (US); Norman V. Scurria, Jr., Elizabeth City, NC (US); Robert C. Roth, Cary, NC (US); Roger C. Sanwald, Raleigh, NC (US); John S. Strenkowski, Cary, NC (US); Leonardo Serra Mattos, Genoa (IT)

(73) Assignees: North Carolina State University, Raleigh, NC (US); DRS C3 & Aviation Company, Herndon, VA (US)

( * ) Notice: Subject to any disclaimer, the term of this patent is extended or adjusted under 35 U.S.C. 154(b) by 478 days.

(21) Appl. No.: 12/534,724

(22) Filed: Aug. 3, 2009

(65) Prior Publication Data

US 2010/0094566 A1    Apr. 15, 2010

Related U.S. Application Data

(60) Provisional application No. 61/085,454, filed on Aug. 1, 2008.

(51) Int. Cl.
*G01B 5/28* (2006.01)
*G06F 11/30* (2006.01)

(52) U.S. Cl.
USPC ............ 702/38; 702/116; 702/182; 702/183; 702/188

(58) Field of Classification Search
USPC .............. 702/38–49, 104, 116–124, 182–189
See application file for complete search history.

(56) References Cited

U.S. PATENT DOCUMENTS

| | | | |
|---|---|---|---|
| 2003/0233876 A1* | 12/2003 | Huang et al. .................... | 73/574 |
| 2005/0146076 A1* | 7/2005 | Alexander et al. ............ | 264/257 |
| 2009/0248366 A1* | 10/2009 | Scheid et al. ................. | 702/188 |
| 2009/0326834 A1* | 12/2009 | Sundaresan et al. ........... | 702/34 |

OTHER PUBLICATIONS

Primary Lithium Battery LS 14500 Datasheet, SAFT, www.saftbatteries.com (Summer 2009).

"Special Use Sensors—Crack Propagation Sensors," Vishay Micro-Measurements, www.vishaymg.com, Document No. 11521 (Feb. 5, 2008).

(Continued)

*Primary Examiner* — Phuong Huynh
(74) *Attorney, Agent, or Firm* — Jenkins, Wilson, Taylor & Hunt, P.A.

(57) ABSTRACT

Methods, systems, and computer readable media for wireless crack detection and monitoring are disclosed. According to one system, a crack detector is affixed to a surface of a material for detecting a crack in the material. In response to detecting a crack, a crack indicator is generated, indicating the existence of the crack. A mote wirelessly communicates the crack indicator to an external device. The mote may also store multiple crack indicators in local memory before being downloaded to the external device.

In other embodiments, the mote may time-stamp the crack indicator for indicating a time when the crack was detected. Additionally, the mote may associate other information with the crack indicator such as temperature and acceleration information.

22 Claims, 4 Drawing Sheets

(56) References Cited

OTHER PUBLICATIONS

"Part 15.4: Wireless Medium Access Control (MAC) and Physical Layer (PHY) Specifications for Low-Rate Wireless Personal Area Networks (WPANs)," IEEE Computer Society (Aug. 31, 2007).

nRF24L01 Single Chip 2.4 GHz Transceiver Datasheet, Nordic Semiconductor (Jul. 2007).

M-Bond AE-15 Datasheet, www.vishaymg.com, Document No. 11012 (Jun. 13, 2007).

M-Coat J Datasheet, www.vishaymg.com, Document No. 11032 (Dec. 7, 2006).

"Special Use Sensors—Crack Detection Sensors," Vishay Micro-Measurements, www.vishaymg.com, Document No. 11520 (Apr. 5, 2006).

Watters et al., "Design and Performance of Wireless Sensors for Structural Health Monitoring," Quantitative Nondestructive Evaluation, AIP Conference Processings, vol. 615, p. 969-976 (2002).

Low-Cost Low-Power 2.4 GHz RF Transceiver CC2500 Datasheet, Texas Instruments (Publication Date Unknown).

Modem PAN 4555 Datasheet, ZigBee™ (Publication Date Unknown).

Vishay Precision Group, "Special Use Sensors—Crack Propagation Sensors," TK-09 Data Sheet, pp. 1-2 (Apr. 7, 2011).

Vishay Precision Group, "Protective Coating," M-Coat J Data Sheet, pp. 1-2 (Jan. 19, 2011).

Vishay Precision Group, "Strain Gage Adhesive," M-Bond 600 Data Sheet, pp. 1-2 (Jun. 24, 2010).

Vishay Precision Group, "Strain Gage Adhesive," M-Bond 43-B Data Sheet, pp. 1-2 (Jun. 24, 2010).

Vishay Precision Group, "Strain Gage Adhesive," M-Bond AE-15 Data Sheet, pp. 1-2 (Jun. 24, 2010).

Vishay Precision Group, "Special Use Sensors—Crack Detection Sensors," Crack Detection Patterns, Micro-Management, pp. 1-3 (Feb. 4, 2010).

* cited by examiner

METHODS, SYSTEMS, AND COMPUTER READABLE MEDIA FOR WIRELESS CRACK DETECTION AND MONITORING

PRIORITY CLAIM

This application claims the benefit of U.S. Provisional Patent Application No. 61/085,454, filed Aug. 1, 2008, the disclosure of which is incorporated herein by reference in its entirety.

TECHNICAL FIELD

The subject matter described herein relates to crack detection and monitoring. More specifically, the subject matter relates to methods, systems, and computer readable media for wireless crack detection and monitoring.

BACKGROUND

Predicting mechanical failure of objects experiencing heavy and/or cyclic loads, such as airplanes, bridges, and trucks, is of great importance to predicting the reliability and safety of these objects. Specifically, objects having a crystalline structure, such as metals, may experience fracture due to fatigue or overload.

Material fatigue includes progressive and localized structural damage that occurs when a material is subjected to cyclic loading. For example, a bridge structure may experience metal fatigue associated with the repeated loading and unloading of vehicle weight across its span.

Material fracture, or cracking, is the local separation of a material into multiple pieces as a result of stress. For example, airplane wings may experience acute and repetitive stress during takeoffs and landings such that metallic or carbon fiber components may become separated or cracked.

Both material fatigue and fracture may result in catastrophic failures of these structures. In many instances, such catastrophic failures may lead to a large loss of human life and therefore is of interest to public safety officials. As a result, scientific disciplines, including fatigue and fracture mechanics, aim at predicting the failure of structures containing cracks, based on detecting the initiation and propagation of cracks, in order to prevent or mitigate these failures before they occur.

One such device for detecting the initiation and propagation of cracks is a crack detector. A crack detector (CD) is a device placed on the surface of a material for detecting when a crack occurs. Typically, crack detectors include a single strand of conductive material forming a closed circuit embedded within a protective film for bonding to the surface of a monitored material. A crack occurring beneath a crack detector will induce local fracture of the strand and open the electrical circuit. The open circuit condition may then indicate a crack in the material which may alert an operator to potential structure failure.

In many industries, structures subject to cracking (i.e., fatigue or fracture) must be inspected in order to comply with safety regulations. However, such inspections are typically manually performed and therefore are tedious, time consuming, and expensive. For example, military aircraft, such as the C-130 cargo plane, are required to be fully inspected for cracks after a predetermined number of flight hours in order to ensure that no stress fractures have occurred that may lead to mechanical failure of a portion of the plane (e.g., wing, fuselage, fuel tank). Also, inspections may serve to ensure that known or pre-existing fractures have not propagated beyond allowable tolerances. Conventional inspections may include dismantling the aircraft in order to physically inspect all surfaces and components for cracks. Experienced inspectors often know locations where cracks are likely to form, whether due to the design of the structure, loading conditions, materials, construction methods, or existing history of cracks.

While the monitoring of certain areas may be aided by the use of conventional crack detectors, not all areas of an airplane may be accessible without a complete manual inspection. For example, airplane fuel tanks may not be accessible for visual crack inspection without dismantling the entire aircraft. Due to these issues, inspection of structures for cracks may nonetheless be a labor intensive process, often requiring six months or more to complete and costing upwards of several million dollars.

One problem associated with using crack detectors to monitor cracks in structures is that the crack detectors must be accessed in order to determine whether a crack has occurred. Accessing a crack detector has conventionally required that the crack detectors be connected via a physical wire to a monitoring device. However, wired connections with each crack detector may be impractical due to electromagnetic interference issues, regulatory constraints, space or structural constraints, and/or the number of crack detectors required. In addition, wired conductors that connect to each crack detector are themselves subject to failure.

Another problem associated with conventional methods for using crack detectors to monitor cracks in surfaces is that the crack detectors themselves have no memory for storing information regarding the occurrence of multiple cracks over time and therefore may not detect a crack that occurs when a structure is expanded and that closes when the structure contracts, i.e., a temporary crack. For example, an airplane cabin may expand when pressurized, causing temporary cracks to form. When the cabin is de-pressurized, the temporary cracks may close. A crack detector positioned at the location of a temporary crack would open when the cabin is pressurized, causing a crack detector signal to be generated and close when the cabin is de-pressurized, terminating the crack detection signal. Without memory or continuous recording of crack occurrences, and unless a crack is detected during cabin pressurization, temporary cracks would be missed.

Accordingly, in light of these difficulties, a need exists for improved methods and systems for wireless crack detection and monitoring.

SUMMARY

Methods, systems, and computer readable media for wireless crack detection and monitoring are disclosed. According to one system, a crack detector is affixed to a surface of a material for detecting a crack in the material. In response to detecting a crack, a crack indicator is generated, indicating the existence of the crack. As used herein, the term "mote" or "sensor node" is a node in a wireless sensor network capable of gathering sensory information, performing limited processing, and communicating information to other nodes in the network. Motes typically include a microcontroller, a transceiver, a memory module, and a power source, and are associated with one or more sensors. A microcontroller may process data and control the functionality of other components in a mote. A transceiver may include the functionality of both a transmitter and a receiver combined into a single device for communicating with other nodes. The power needed by a mote for performing sensing, communication and data processing functions may be supplied by a power source associated with each mote, such as a battery. Distributed motes then wirelessly communicate the crack indicator to an external device. The mote may also store multiple crack indicators in local memory before being downloaded to the external device.

In other embodiments, the mote may time-stamp the crack indicator to indicate a time when the crack was detected. Additionally, the mote may associate other information with the crack indicator such as temperature and acceleration information.

A method for wireless crack detection and monitoring is also disclosed. The method includes detecting a crack in a material and generating a crack indicator, indicating the existence of the crack. The crack indicator is then wirelessly communicated to a remote device. In other embodiments, the crack indicator may then be associated with a time-stamp, acceleration, or temperature value.

The subject matter described herein for wireless crack detection and monitoring may be implemented using a computer readable medium having stored thereon computer executable instructions that, when executed by a computer processor, perform the steps described herein for wireless crack detection and monitoring. Exemplary computer readable media suitable for implementing the subject matter described herein include disk memory devices, programmable logic devices, and application specific integrated circuits. In one implementation, the computer readable medium may include a memory accessible by a processor. The memory may include instructions executable by the processor for implementing any of the methods for routing a call described herein. In addition, a computer readable medium that implements the subject matter described herein may be distributed across multiple physical devices and/or computing platforms.

BRIEF DESCRIPTION OF THE DRAWINGS

The subject matter described herein will now be explained with reference to the accompanying drawings of which.

DETAILED DESCRIPTION

Figure 1:
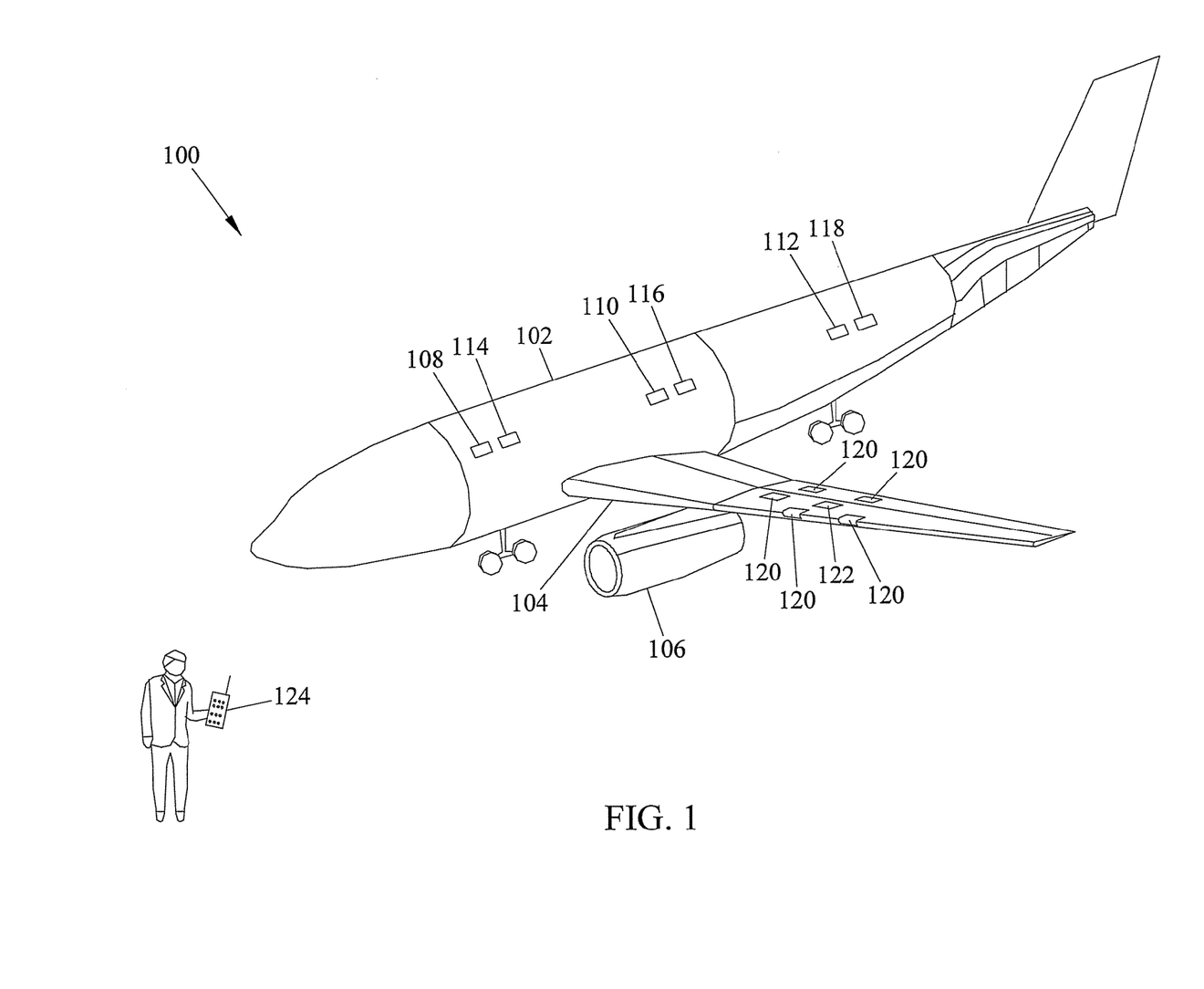
FIG. 1 is a perspective view of an aircraft, illustrating exemplary placement of wireless crack detectors and motes according to an embodiment of the subject matter described herein.

FIG. 1 is a perspective view of an aircraft, illustrating an exemplary placement of wireless crack detectors and motes for detecting and monitoring cracks according to an embodiment of the subject matter described herein. Referring to FIG. 1, aircraft 100 may include any aircraft for which crack detection and monitoring is desired. Aircraft 100 may include metal and/or carbon fiber materials for forming the structural components and/or the skin. One example of aircraft 100 may include the C-130 military cargo plane; however, all sizes of both commercial and military aircraft are intended to be within the scope of the subject matter described herein. Moreover, aircraft 100 is merely intended as an exemplary object for which crack detection and monitoring may be desired. Other objects suitable for wireless crack detection and monitoring may include bridges, vehicles and vessels, such as, tanks, trucks, and ships, buildings and construction equipment.

Aircraft 100 may include various points of interest being susceptible to cracking under various loading conditions. For example, aircraft 100 may include fuselage 102, wing 104, and engine 106 and having different materials and mechanical stresses associated with each. Therefore, a plurality of crack detectors and motes may be bonded to the surface of structural components of fuselage 102 for detecting and monitoring cracks and transmitting information to an operator for analysis. In one configuration, crack detectors 108, 110, and 112 may be placed at predetermined intervals along fuselage 102, and may be paired with motes 114-118, respectively.

In another configuration, multiple crack detectors may be located in proximity to one another and associated with a single mote, forming a cluster. Such a configuration may be advantageous in an area in which several cracks are likely to form and/or more focused monitoring is desired. For example, plurality of crack detectors 120 may be associated with mote 122 to form a cluster.

It is appreciated that crack detectors 108-112 and 120 may be placed at locations likely to crack. The likelihood of a particular location to experience mechanical failure, whether from fatigue or fracture, may be determined based on, for example, design flaws and/or limitations, loading conditions, materials, construction methods, and previous history of cracks. On aircraft, such locations are known by aircraft mechanics, and this knowledge can be used to optimize crack detector placement. For example, aircraft mechanics may know that locations where the wings attach to the fuselage are likely to crack, and thus, crack detectors may be placed in such locations.

Crack detectors 108-112 and 120 may detect the existence of cracks in a material. For example, crack detectors 108-112 and 120 may each form an electrical circuit such that either an open circuit condition or a closed circuit condition may be detected when electric current is transmitted through the crack detector. An open circuit condition may be created in one of crack detectors 108-112 and 120 if the underlying material to which the crack detector is bonded separates such that a conductive filament within the crack detector also becomes separated. Conversely, if no separation in the underlying material exists, the crack detector filament will remain intact and form a closed circuit (i.e., its default state). These open or closed circuit conditions may therefore be used to generate a crack detection signal, referred to herein as a "crack indicator," for indicating the presence of a crack.

The crack indicator(s) may be temporarily stored by motes 114-118 and 122 (i.e., for detecting cracks occurring during a flight) and may be wirelessly communicated to an external device for analysis. For example, information stored in motes 114-118 and 122 during a flight may be transmitted to portable data assistant (PDA) 124 or another portable device. In one embodiment, PDA 124 may include a transceiver for communicating with corresponding wireless transceivers included in each mote in order to receive crack indictors and any other information gathered during the flight.

According to one feature of the subject matter described herein, motes 114-118 and 122 may time-stamp crack indicators for determining a time or time period during which the crack occurred. For example, crack detectors 108-112 and 120 may generate crack indicators any time a crack forms, and these indicators may be time-stamped and stored by motes 114-118 and 122. In addition, motes 114-118 and 122 may periodically or aperiodically poll crack detectors 108-112 and 120 to detect crack formation.

Thus, each of motes 114-118 and 122 may store a history of crack formation over time for the respective crack detector(s) with which the mote communicates. Such a history may be used to detect temporary cracks. For example, at a given crack detector, a crack occurrence history may include a positive crack indicator for a first time-stamp, and a negative crack indicator for a subsequent time-stamp, thus indicating the presence of a temporary crack.

Based on the power source, antenna, frequency, location, materials, and other factors, the range over which data may be transmitted between motes 114-118, 122 and PDA 124 may vary. Typical ranges may include up to approximately 25 meters. Therefore, a technician may gather information for motes 114-118 and 122 by walking PDA 124 around aircraft 100. PDA 124 may include a user interface (UI) for aiding the technician in ensuring that all motes 114-118 and 122 are functioning properly and have transmitted data, as well as alerting the operator of cracks which have occurred or propagated between evaluations. The data may be exported from PDA 124 into a variety of formats including, but not limited to, Microsoft Excel™ format for further analysis.

Advantages of the system described herein for wirelessly detecting and monitoring cracks includes simplicity of design, installation, and use. Crack detectors 108-112, 120 and motes 114-118, 122 may be installed when a structure is in its operational environment and without taking the structure out of service (i.e., when an airplane is on the ground, a bridge in place, etc.) and therefore may be applied to pre-existing structures most likely to require crack monitoring. Installation in an operational environment also requires minimal disruption to conventional service schedules and procedures. Furthermore, individual crack detectors and/or motes may be easily added or replaced without disrupting other elements in the sensor network. Due to this simplicity, the system described herein may be small and lightweight (i.e., 1 oz with battery) thereby allowing for application in small spaces, low cost and low power (i.e., greater than 5 year battery life).

Another advantage of the system described herein for wirelessly detecting and monitoring cracks includes reliability. Transceiver 208 (FIG. 2) may provide reliable bidirectional communication at 25 meters, even in suboptimal environments. Because there is no single point of failure in the distributed data network described herein, an accurate assessment of a structure may still be possible after suffering some node failures. Moreover, as the number of nodes increases, so does the robustness of the network.

Another advantage of the system described herein for wirelessly detecting and monitoring cracks includes providing a wealth of data. Because a precise time/date stamp is associated with each crack indicator, detection of different types or severities of cracks is enabled. Each mote 114 may monitor multiple crack detectors 108 in various cluster configurations. Additionally, mote 114 may be associated with additional sensors, for example, temperature and 3-axis acceleration data.

Figure 2:
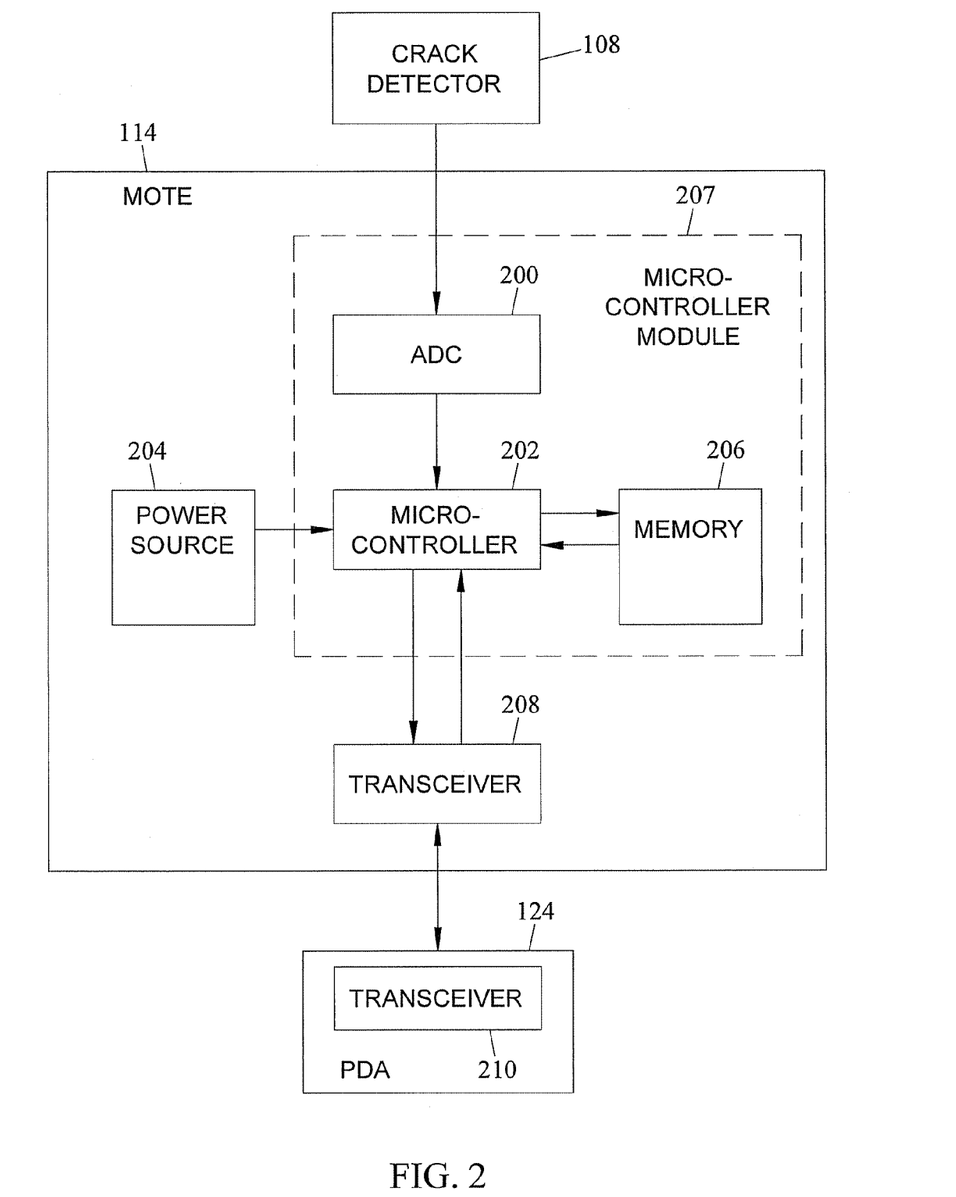
FIG. 2 is a block diagram of an exemplary system for wirelessly detecting and monitoring cracks in a material according to an embodiment of the subject matter described herein.

FIG. 2 is a block diagram of an exemplary system for wirelessly detecting and monitoring cracks in a material according to an embodiment of the subject matter described herein. Referring to FIG. 2, crack detector 108 may include any suitable crack detection sensor or gage for indicating the presence of a crack or indicating when a crack has progressed to a predetermined location on a structure. The rate of crack growth may be monitored through the use of multiple crack detectors or through specialized crack propagation detectors having multiple conductive elements.

In one embodiment, crack detector 108 may include a crack sensor consisting of a single strand of copper or a high endurance alloy embedded in a protective material and bonded to the surface of a material. For example, a beryllium copper alloy may be laminated to a polyimide for maximum conformability to irregular surfaces. Alternatively, an isoelastic alloy may be laminated to a glass-fiber-reinforced backing for applications where superior durability is needed due to high cyclic strains. One commercially available crack detector includes the CD-series™ gages produced by Vishay Micro-Measurements® of Malvern, Pa. Specifically, the CD-02™ series and the CD23™ series gages are available in various strand lengths ranging from 10 mm to 50 mm and resistances ranging from 0.05 Ω/mm to 1 Ω/mm of active strand length.

Before adhering the crack detector to the material surface, the surface may be cleaned in order to promote proper bonding. For example, chemical solvents may be used to prepare the surface for bonding. However, these solvents may be harmful to the environment and difficult to use. Therefore, non-chemical means, such as a plasma pen, may be used to prepare a surface for bonding. For example, chromate primed aluminum may be cleaned using a plasma pen having a one millimeter gap between the nozzle of the pen and the surface of the aluminum, while removing any oxidized residue after every few passes of the plasma pen.

After cleaning, the crack detector may be adhered to the material surface using a suitable bonding agent. For example, one commercially available adhesive includes M-Bond AE-15™ produced by Vishay Micro-Measurements® of Malvern, Pa. Alternatively, M-Bond 600™ or M-Bond 43-B™, produced by Vishay Micro-Measurements, may be suitable for bonding crack detectors to surfaces over a wide operating temperature range.

A protective coating may also be applied to the crack detector for preventing corrosion, which can cause premature filament failure. For example, M-Coat J™ produced by Vishay Micro-Measurements® of Malvern, Pa. is a commercially available protective coating suitable for protecting crack detectors from atmospheric corrosion and other contamination.

In addition to the single-filament crack detector described above, multi-filament crack detectors may also be used without departing from the scope of the subject matter described herein. Multi-filament crack detectors may consist of a number of resistor strands connected in parallel for indicating the rate of crack propagation in a structure. As a surface crack progresses though each strand in the crack detector filament pattern, successive open-circuits are created, thereby increasing the total resistance of the detector. Resistor strands may operate independently, each producing an open circuit when fractured. This may allow the crack detector to electrically predetermine a specific point in the fracturing process at which the detector will generate an alert. One example of a commercially available multi-filament crack propagation detector includes the TK-09™ series produced by Vishay Micro-Measurements® of Malvern, Pa. Another type of multi-element crack detector may consist of independent concentric strands forming arcs customized to the desired geometry, where distance and direction of crack travel is indicated by which strands are open-circuited.

Crack detector 108 may be connected to mote 114 using any suitable means. For example, a wired interconnection may be used for transmitting power to and communicating with crack detector 108. Crack detector 108 and mote 114 are bonded to the structure being monitored for cracks, and, due to their proximity to one another, may be connected to each other via traces or wires.

Referring to mote 114, analog-to-digital converter (ADC) 200 may include an electronic integrated circuit for converting continuous signals to discrete digital numbers. For example, ADC 200 may be an electronic device for converting an input analog voltage (or current) to a digital number. The digital output may be using different coding schemes, such as binary. In one embodiment, an analog signal from crack detector 108 may be of a level that indicates the presence or absence of a crack and converted to a digital signal by ADC 200. In other embodiments, ADC 200 may be eliminated and signals from crack indicator 108 may be directly received and interpreted by microcontroller 202.

Microcontroller 202 may be a device containing a processor, memory, and input/output functions. In addition to arithmetic and logic elements, microcontroller 202 may integrate additional elements such as read-write memory for data storage, read-only memory for program storage, EEPROM for permanent data storage, peripheral devices, and input/output interfaces. Microcontroller 202 may operate at very low speed and consume relatively little power (milliwatts). Additionally, microcontroller 202 may be configured to operate in a "sleep" mode while awaiting input, thus making it ideal for low power and long lasting battery applications. Microcontroller 202 may execute programs for polling crack detector 108 and for time-stamping and storing crack indicators generated by crack detector 108.

Power source 204 may include one or more batteries. For example, batteries may include Lithium Thionyl Chloride AA batteries selected for high power density and low weight. One commercially available example of a battery 204 suitable for powering microcontroller 202 includes the LS14500 series of batteries produced by Saft Corporation headquartered in Bagnolet, France.

Memory 206 may include any suitable volatile or nonvolatile memory for storing crack indicator information. This may include random access memory (RAM), flash memory, solid state disks (SSD), etc., without departing from the scope of the subject matter described herein. It is appreciated that ADC 200, microcontroller 202, and memory 206 may collectively form microcontroller module 207. Microcontroller module 207 may include an integrated circuit chip or any other electronic packaging suitable for use in mote 114.

Transceiver 208 may include the functionality of both a transmitter and a receiver combined into a single device. Transceiver 208 may use radio frequency (RF) communication for sending and receiving data at frequencies between about 433 MHz and 2.4 GHz; however, other communications methods, such as optical communications (i.e., lasers) and infrared communications, may also be used without departing from the scope of the subject matter described herein.

One commercially available example of transceiver 208 is the CC2500 transceiver, a Chipcon product by Texas Instruments of Dallas, Tex. The CC2500 is a single chip, low power 2.4 GHz RF transceiver. The CC2500 has 64 byte reception and transmission buffers and an effective data rate of 250 kbps. The CC2420 can also be used.

Another commercially available example of transceiver 208 is the nRF24L01 transceiver produced by Nordic Semiconductor Corporation of Trondheim, Norway. The nRF24L01 is a single chip ultra high frequency (UHF) transceiver operating in the 433 MHz industrial, scientific, and medical (ISM) frequency band. It includes frequency shift keying (FSK) modulation and demodulation, has a bit rate of 20 kbps and a transmission power of up to 10 dBm, and is powered by a single +3-5V DC power supply.

A third commercially available example of transceiver 208 is the PAN4555 manufactured by Panasonic Industrial Components of Secaucus, N.J. The PAN4555 is a short range, low power, 2.4 GHz single chip transceiver. It operates in the ISM frequency band, using direct sequence spread spectrum (DSSS) modulation, and contains a complete IEEE 802.15.4 physical layer (PHY) modem to comply with the IEEE 802.15.4 wireless standard. The PAN4555 chip also includes Freescale's MC13213 microcontroller with reference oscillator, but SMAC, MAC, or ZigBee Bee-Stack from Freescale can be used in place of the MC13213. This Panasonic chip can be scaled to fit applications ranging from simple point to point systems to ZigBee networking and complies to EN300328, FCC CFR Part 15 and ARIB STD-T66.

PDA 124 may include any suitable external electronic device for receiving data recorded by crack monitors. PDA 124 may include a transceiver 210 for communicating with transceiver 208 located at each mote 114 during an interrogation of crack detector 108 while the object to be monitored for cracks is in its operational environment (e.g., parked in a hangar between flights). One commercially available example of PDA 124 suitable for connecting with a transceiver and for interrogating mote 114 is the iPAQ™ manufactured by Hewlett Packard (HP) of Palo Alto, Calif. However, it is appreciated that any laptop, subnotebook, tablet, desktop PC, or application specific handheld device may also be used without departing from the scope of the subject matter described herein.

Figure 3A:
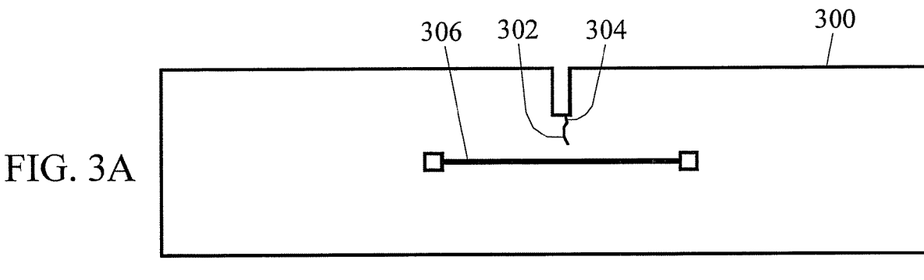
FIGS. 3A, 3B, and 3C are plan views of a surface being monitored for cracks, illustrating detection and propagation of a crack according to an embodiment of the subject matter described herein.
Figure 3B:
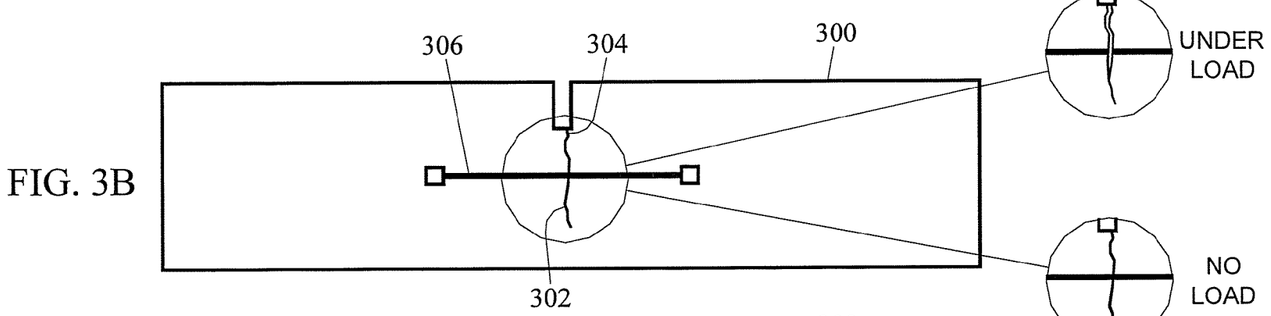
Figure 3C:
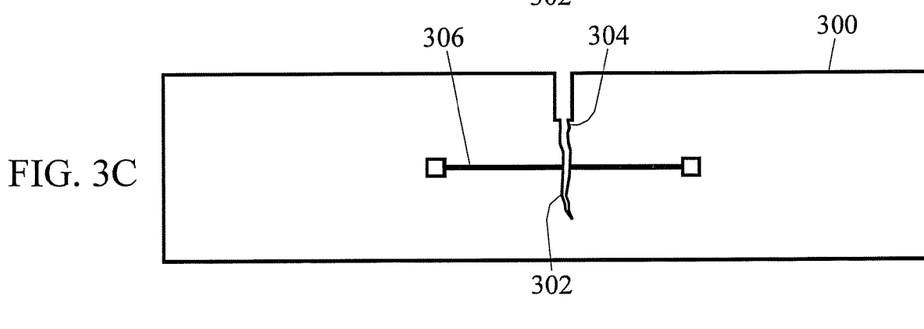

FIGS. 3A, 3B, and 3C are plan views of a surface being monitored for cracks, illustrating the detection of crack initiation and propagation in a material according to an embodiment of the subject matter described herein. Referring to FIG. 3A, material 300 may include crack 302 to be monitored. Crack 302 may begin at initiation site 304 and be visible to an observer of the surface of material 300. Crack detector 306 may be placed on material 300 for detecting when crack 302 has separated material 300 at a location of interest, such as for inspection, maintenance, performance, or safety purposes. However, in FIG. 3A the monitored location has not experienced a crack.

In FIG. 3B, crack 302 has propagated into material 300 thus forming a longer crack and extending beneath crack detector 306. The monitored location has experienced a crack in its early stages under load, which closed upon load removal, indicating insufficient displacement of failed material to permanently open crack detector 306. It is appreciated that material 300 may become separated, connected, and reseparated (i.e., crack 302 is created, closed, and opened again) many times due to, for example, cyclic stresses on material 300. Because crack detector 306 may detect both an open circuit condition and/or a closed circuit condition, each crack instance may be detected and recorded.

In FIG. 3C, crack 302 is shown to have widened, resulting in permanent separation of both material 300 and crack detector 306. As such, separation of material 300 results in an open circuit condition that may be recorded as a detected crack and optionally associated with time-stamp, acceleration, temperature, or other data. Additionally, mote 114 in FIG. 2 may poll crack detector 306 for cracks at predetermined intervals. In addition to single crack detector 306, a specialized crack propagation detector (not shown) including multiple filaments may also be used for detecting propagation of crack 302 without departing from the scope of the subject matter described herein.

Figure 4:
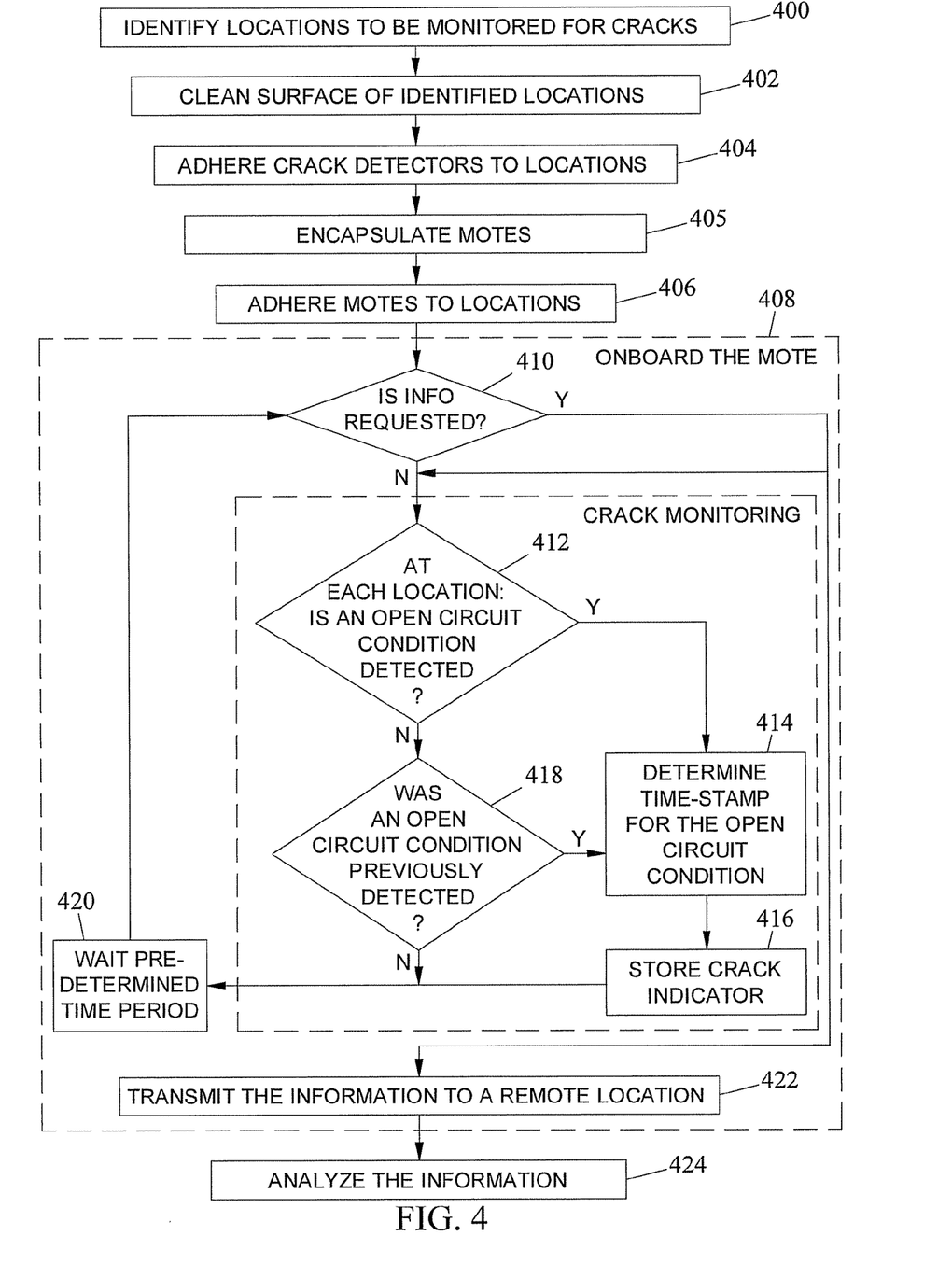
FIG. 4 is a flow chart of an exemplary process for wirelessly detecting and monitoring cracks in a material according to an embodiment of the subject matter described herein.

FIG. 4 is a flow chart of exemplary steps for wirelessly detecting and monitoring cracks in a material according to an embodiment of the subject matter described herein. Referring to FIG. 4, in block 400, the locations to be monitored for cracks are identified. For example, locations likely to form cracks may be known, whether due to the design of the structure, its loading conditions, materials used, construction methods, or an existing history of cracks.

In block 402, the surfaces of the locations to be monitored are cleaned/prepared so that motes and crack detectors will properly bond with the surface for accurate detection of cracks under a variety of stresses and operating conditions. These may include extreme G-forces and temperatures, for example, when attached to airplanes for monitoring surfaces during flight.

In block 404, one or more crack detectors may be adhered to locations on the object to be monitored.

In block 405, motes may be encapsulated in order to be protected from the physical environment. For example, a protective polymer (e.g., urethane) or other material may surround motes in order to prevent or reduce, for example, corrosion due to extreme environmental conditions including temperature changes, moisture, and ultraviolet radiation.

In block 406, one or more motes may also be adhered to locations on the object to be monitored. It is appreciated that in addition to a 1:1 association of crack detectors and motes, multiple crack detectors may be located close together and associated with a single mote, forming a cluster. Such a configuration may be advantageous in areas in which many cracks are likely to form and more focused monitoring is desired.

In block 408, the material may be monitored for cracks. In block 410, it is determined whether information is requested from a mote by a remote device, such as a PDA. For example, requested information may include one or more crack indicators and associated time-stamps. If information is requested, the stored information may be transmitted to a remote location for analysis as in block 422. For example, a PDA may collect information from a plurality of motes located on a monitored object. Thus, the loop shown in block 410 indicates that each mote continuously awaits information requests from the remote device before transmitting the information.

Whether or not information has been requested by a remote device, control proceeds to block 412 where, at each location on the surface of the material, it is determined whether an open circuit condition exists at a crack detector. If an open circuit condition is detected, indicating a separation in the material (i.e., a crack), control proceeds to block 414. If no open circuit condition is detected, but an open circuit condition was previously detected, control also proceeds to block 414.

In block 414, a time and/or date may optionally be associated with the crack indicator detected in blocks 412 and 418. It is appreciated that crack detectors and/or motes may automatically detect an open circuit condition as soon as it occurs or may be monitored (i.e., periodically or aperiodically polled) at predetermined intervals for determining whether a previously detected crack exists. Once a time-stamp has been determined for an open circuit condition, control proceeds to block 416.

In block 416, the time-stamped crack indicator information may be stored locally, for example, in a memory of a mote, for later retrieval. After the time-stamped crack indicator is stored, control proceeds to block 420.

In block 420, once crack indicators have been stored or if no open circuit condition was previously detected in block 418, a predetermined time interval elapses before polling the crack detector again (i.e., return to block 410). In this way, by configuring the polling time interval in block 420, a balance between temporal accuracy of crack indicator data and power consumption may be achieved.

Returning to block 422, after information is transmitted to a remote location, control proceeds to block 424. In block 424, the information may be analyzed offsite in order to determine, among other things, the likelihood of mechanical failure, the necessity for further inspection, and identification of possible design and/or manufacturing defects.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A system for wireless crack detection and monitoring, the system comprising:
a plurality of crack detectors configured to be attached to a plurality of different user-selected locations likely to experience cracks on a surface of a material of a pre-existing structure in its operational environment for detecting cracks in the material, wherein each crack detector comprises a single sensor configured to generate, by itself, a crack indicator in response to formation of a crack at its respective location and wherein the crack detectors collectively form a sensor network; and
a plurality of motes configured to be attached to the surface of the pre-existing structure in its operational environment, wherein each of the motes is paired with at least one of the crack detectors for receiving the crack indicator from the crack detector and wirelessly communicating the crack indicator to a remote device indicating the presence of a crack at the location of the corresponding crack detector.

2. The system of claim 1 wherein the mote is configured to associate a time-stamp with the crack indicator.

3. The system of claim 1 wherein the crack detector includes a single-filament detector for detecting initiation of the crack.

4. The system of claim 1 wherein the crack detector includes a multi-filament detector for detecting propagation of the crack.

5. The system of claim 1 wherein the mote is configured to store the information locally.

6. The system of claim 1 wherein the mote is configured to communicate the information to one of a laptop computer, a desktop computer, and a personal digital assistant (PDA).

7. The system of claim 1 wherein the mote includes a transceiver.

8. The system of claim 6 wherein the transceiver operates using radio frequency (RF).

9. The system of claim 1 wherein the mote includes a microcontroller.

10. The system of claim 1 wherein the mote includes a memory.

11. The system of claim 1 wherein the mote polls the crack detector periodically or aperiodically.

12. The system of claim 1 wherein the mote polls the crack detector, stores a history of signals generated by the crack indicator, and presents the history to a user.

13. The system of claim 9 wherein the memory includes one of random access memory (RAM) and flash memory.

14. The system of claim 1 wherein the mote includes a power source.

15. The system of claim 1 wherein the power source includes one of a battery, a solar cell, and an energy harvester.

16. The system of claim 1 wherein the mote includes an analog-to-digital converter (ADC).

17. A method for wireless crack detection and monitoring, the method comprising:
   attaching a plurality of crack detectors to a plurality of different user-selected locations likely to experience cracks on a surface of a pre-existing structure in its operational environment;
   attaching motes to the surface of the material of the pre-existing structure in its operational environment, wherein each of the motes is paired with at least one of the crack detectors;
   detecting, by individually using the crack detectors, cracks in the material at the user-selected location;
   generating a crack indicator, indicating the existence of the crack, wherein each crack detector comprises a single sensor configured to generate, by itself, a crack indicator in response to formation of a crack, at its respective location and wherein the crack detectors collectively form a sensor network; and
   wirelessly communicating, using the motes, the crack indicators to a remote device indicating the presence of a crack at the location of the corresponding crack detector.

18. The method of claim 17 comprising associating a time-stamp with the crack indicator.

19. The method of claim 17 comprising storing the information locally.

20. The method of claim 17 comprising polling a crack detector, generating a history of time-stamped crack indicators, and presenting a history to a user.

21. A method for adhering a crack detector and mote to the surface of a material, the method comprising:
   cleaning a surface of a material of a pre-existing structure to be monitored for cracks;
   bonding a plurality of crack detectors to a plurality of different user-selected locations likely to experience cracks on the surface of the material of the pre-existing structure in its operational environment, wherein the crack detectors collectively form a sensor network;
   bonding a plurality of motes associated with the crack detector to the surface of the material of the pre-existing structure in its operation environment, wherein each of the motes is paired with at least one of the crack detectors and wherein each mote is attached to the surface;
   applying a protective coating over the plurality of crack detectors and the plurality of motes; and
   detecting a crack in the material at the user-selected location by individually using the crack detector and wirelessly communicating an indication of the crack to an external device using the mote indicating the presence of a crack at the location of the corresponding crack detector.

22. A non-transitory computer readable medium containing computer executable instructions stored therein for causing a computer to perform steps comprising:
   attaching a plurality of crack detectors to a plurality of different user-selected locations likely to experience cracks on a surface of a pre-existing structure in its operational environment;
   attaching motes to the surface of the material of the pre-existing structure in its operational environment, wherein each of the motes is paired with at least one of the crack detectors;
   detecting, by individually using the crack detectors, cracks in the material at the user-selected location;
   generating, using the crack detector, a crack indicator, indicating the existence of the crack, wherein each crack detector comprises a single sensor configured to generate, by itself, a crack indicator in response to formation of a crack at its respective location and wherein the individual crack detectors form a sensor network; and
   wirelessly communicating, using the motes, the crack indicators to a remote device indicating the presence of a crack at the location of the corresponding crack detector.

* * * * *